United States Patent [19]

Alvarez

[11] 4,198,336

[45] Apr. 15, 1980

[54] CHEMICAL PROCESS FOR PREPARING ANDROSTA-4-ENE 17α-CARBOXYLIC ACIDS

[75] Inventor: Francisco S. Alvarez, Sunnyvale, Calif.

[73] Assignee: Syntex (U.S.A.) Inc., Palo Alto, Calif.

[21] Appl. No.: 893,642

[22] Filed: Apr. 5, 1978

[51] Int. Cl.$^2$ ................................................. C07J 1/00
[52] U.S. Cl. .......................... 260/239.55 D; 260/397.1; 260/239.5; 260/397.45
[58] Field of Search .................... 260/397.1, 239.55 D; /Steroids MS File

[56] References Cited

U.S. PATENT DOCUMENTS

| | | | |
|---|---|---|---|
| 3,828,080 | 8/1974 | Phillipps et al. | 424/242 |
| 4,119,625 | 10/1978 | Schmidlin | 260/397.1 |

OTHER PUBLICATIONS

"Steroid Reactions" by Djerassi, (1963).
"Organic Reactions in Steroid Chemistry", (1972), by Fried et al., p. 148.

*Primary Examiner*—Elbert L. Roberts
*Attorney, Agent, or Firm*—Tom M. Moran; Gerard A. Blaufarb

[57] ABSTRACT

This invention is a process for preparing 3-keto-androst-4-ene 17α-carboxylic acids, androsta-1,4-diene 17α-carboxylic acids and their 17α-esters by reacting a corresponding 21-hydroxypregn-4-ene-3,20-dione, 21-hydroxypregna-1,4-diene-3, 20-dione, or their 21-esters with an alkali metal carbonate base in a lower alkanol in the presence of oxygen. The 17α-esters are formed by reacting the 17α-carboxylic acid with a suitable alkylating agent.

14 Claims, No Drawings

CHEMICAL PROCESS FOR PREPARING ANDROSTA-4-ENE 17α-CARBOXYLIC ACIDS

BACKGROUND OF THE INVENTION

1. Field of the Invention

This invention relates to a process for preparing androst-4-ene 17β-carboxylic acids. More particularly, it relates to a process for preparing androst-4-ene 17β-carboxylic acid by reacting a 21-hydroxy (or a 21-ester) pregn-4-ene-3,20-dione with an inorganic base such as potassium carbonate in an oxygenated hydrocarbon solvent such as methanol in the presence of oxygen to form the desired androst-4-ene 17β-carboxylic acid.

2. Prior Art

It is known that 3-oxoandrost-4-ene 17β-carboxylic acids can be prepared by treating a 3,20-diketopregn-4-ene with sodium hypobromite in a suitable solvent. See, for example, U.S. Pat. No. 2,769,822 to Gash of Monsanto. It is also known that an ester can be hydrolysed to an acid by refluxing with methanol and potassium carbonate under nitrogen.

Surprisingly, it has now been discovered that a 21-hydroxy-20-ketopregn-4-ene or a 21-ester-20-ketopregn-4-ene can be converted to the corresponding androst-4-ene 17β-carboxylic acid by reacting the 20-ketopregn-4-ene with a suitable inorganic base such as potassium carbonate in an oxygenated hydrocarbon solvent such as methanol in the presence of oxygen at low temperatures.

SUMMARY OF THE INVENTION

In summary, this invention is a process for preparing an androst-4-ene 17α-carboxylic acid chosen from those represented by formula (II) in Reaction Sequence 1, below, wherein $X^1$ is hydrogen, fluoro, chloro or bromo;
$X^2$ is hydrogen, fluoro or chloro;
$X^3$ is hydrogen or is fluoro when $X^2$ is fluoro and $X^1$ is hydrogen;
$X^4$ is hydrogen, fluoro, chloro or bromo;
$X^5$ is

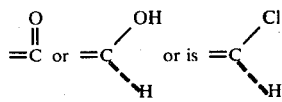

when $X^4$ is chloro;
$X^4$ and $X^5$ together represent an additional bond between C-9 and C-11;
$R^1$ is hydroxy or is alkanoyloxy of 2–6 carbons when $R^2$ is α-methyl, β-methyl or hydrogen;
$R^1$ and $R^2$ together are isopropylidenedioxy; and the solid and broken lines between C-1 and C-2 represent a single or double bond;
which process comprises reacting a compound represented by formula (I) in Reaction Sequence 1 wherein
R is hydrogen or lower alkanoyl of 2–6 carbons or benzoyl and $X^1$, $X^2$, $X^3$, $X^4$, $X^5$, $R^1$ and $R^2$ are as described hereinbefore, with an inorganic base such as an alkali metal carbonate and an oxygenated hydrocarbon such as a lower alkanol in the presence of oxygen to form the corresponding compounds of formula (II) wherein $X^1$, $X^2$, $X^3$, $X^4$, $X^5$, $R^1$ and $R^2$ are as previously defined.

Preferably the alkali metal carbonate is sodium carbonate or potassium carbonate, the lower alkanol is methanol, and the oxygen is provided by injecting air into the reaction mixture.

The compounds formed by the process of this invention are useful as topical anti-inflammatory agents or intermediates therefor.

PREFERRED EMBODIMENTS

The process of this invention is represented by the following Reaction Sequence 1:

REACTION SEQUENCE 1

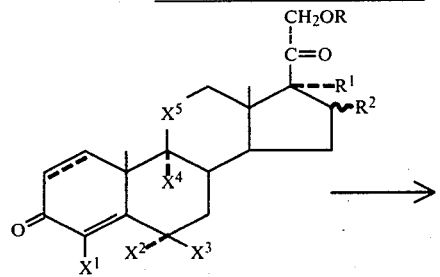

(I)

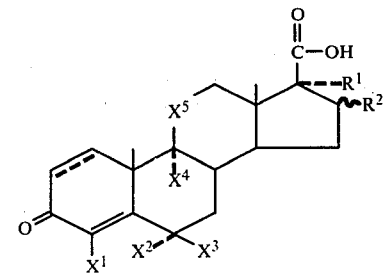

(III)

wherein $X^1$ is hydrogen, fluoro, chloro or bromo;
$X^2$ is hydrogen, fluoro or chloro
$X^3$ is hydrogen or is fluoro when $X^2$ is fluoro and $X^1$ is hydrogen;
$X^4$ is hydrogen, fluoro, chloro or bromo;
$X^5$ is

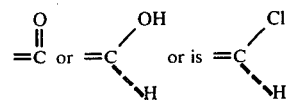

when $X^4$ is chloro;
$X^4$ and $X^5$ together represent an additional bond between C-9 and C-11;
R is hydrogen, alkanoyl of 1–6 carbons or benzoyl;
$R^1$ is hydroxy or is alkanoyloxy of 2–6 carbons when $R^2$ is α-methyl, β-methyl or hydrogen;
$R^1$ and $R^2$ together are isopropylidenedioxy; and the solid and broken lines between C-1 and C-2 represent a single or double bond.

The process is particularly valuable for converting compounds of formula (I) wherein
$X^1$ and $X^2$ are independently hydrogen, fluoro or chloro and $X^3$ is hydrogen or fluoro when $X^2$ is fluoro and $X^1$ is hydrogen (especially when $X^3$ is hydrogen)

$X^4$ is hydrogen, fluoro or chloro;
$X^5$ is

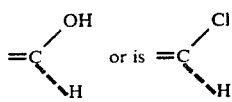

when $X^4$ is chloro;
R is hydrogen or alkanoyloxy of 2-6 carbon atoms;
$R^1$ is hydroxy when $R^2$ is α-methyl;
$R^1$ and $R^2$ together are isopropylidenedioxy; and
the broken and dotted lines between the 1- and 2-positions of the steroid ring represent a double bond.

Of these preferred compounds, the process is particularly preferred for those compounds wherein $R^1$ is hydroxy and $R^2$ is α-methyl.

The process of this invention to convert a compound of formula (I) into a compound of formula (II) is carried out in a suitable oxygenated hydrocarbon solvent such as a lower alkanol. Particularly valuable and, therefore preferred are methanol and ethanol, particularly the former. The reaction medium is made slightly basic by the inclusion of a suitable weak inorganic base such as an alkali metal carbonate, for example sodium, lithium or potassium carbonate. Potassium carbonate is preferred. The conversion of a compound of formula (I) to a compound of formula (II) takes place at temperatures of about 10° C. to about the boiling of the solvent being employed, e.g., about 75° C. for ethanol and about 50° C. for methanol. Generally, however, the reaction readily takes place from ambient temperatures, i.e., about 20° C.-25° C.

An important aspect of the process of this invention is the presence of oxygen during the reaction. Oxygen can be supplied to the reaction mixture by a variety of ways. For example the reaction mixture can be stirred vigorously in a reaction vessel open to the air so that air is mixed with the reaction mixture. This is relatively inefficient however, thus it is preferred that oxygen be injected into the reaction mixture. This is readily accomplished by bubbling a stream of air or oxygen, preferably the former, into the reaction mixture while it is being stirred. The reaction at ambient temperatures will be complete about 1 to 48 hours, depending on the reactants. Less time is required at higher temperatures.

STARTING MATERIALS

Many starting materials useful in the process of this invention are well known, such as corticosterone, dehydrocorticosterone, hydrocortisone, prednisone, cortisone, paramethasone, betamethasone, dexamethasone, prednisolone, flumethasone, triamcinolone acetonide, fluocinolone acetonide, the corresponding 21-esters and the like.

Other starting materials, represented by formula (I) wherein $X^5$ is

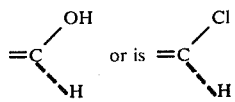

when $X^4$ is chloro; $X^1$ and $X^4$ are independently fluoro, chloro or bromo; $X^2$ is fluoro or chloro; $X^3$ is hydrogen or is fluoro when $X^2$ is fluoro and $X'$ is hydrogen and R is an acyl group are readily prepared by starting with compounds known in the art proceeding according to Reaction Sequences 2 or 3.

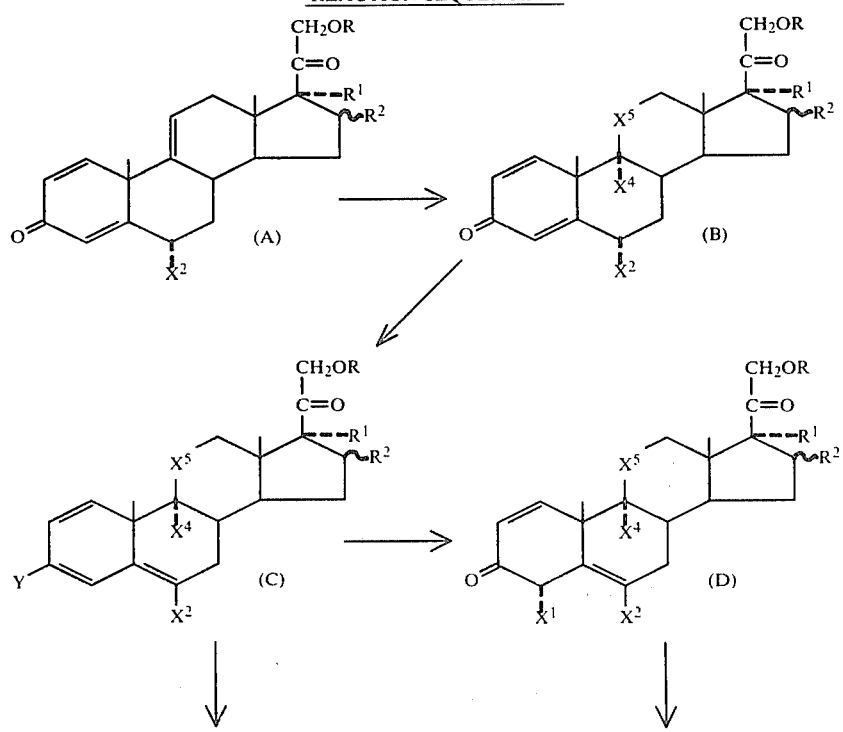

REACTION SEQUENCE 2

REACTION SEQUENCE 2

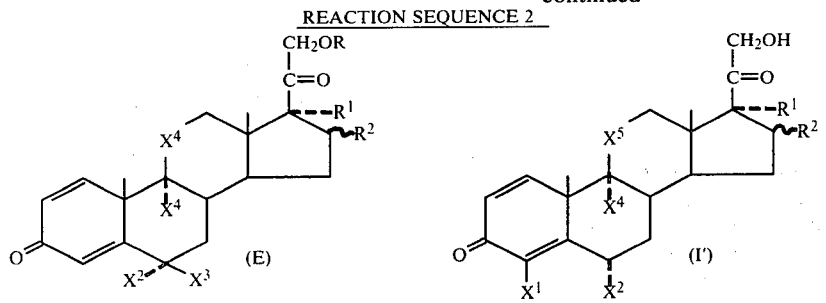

REACTION SEQUENCE 3

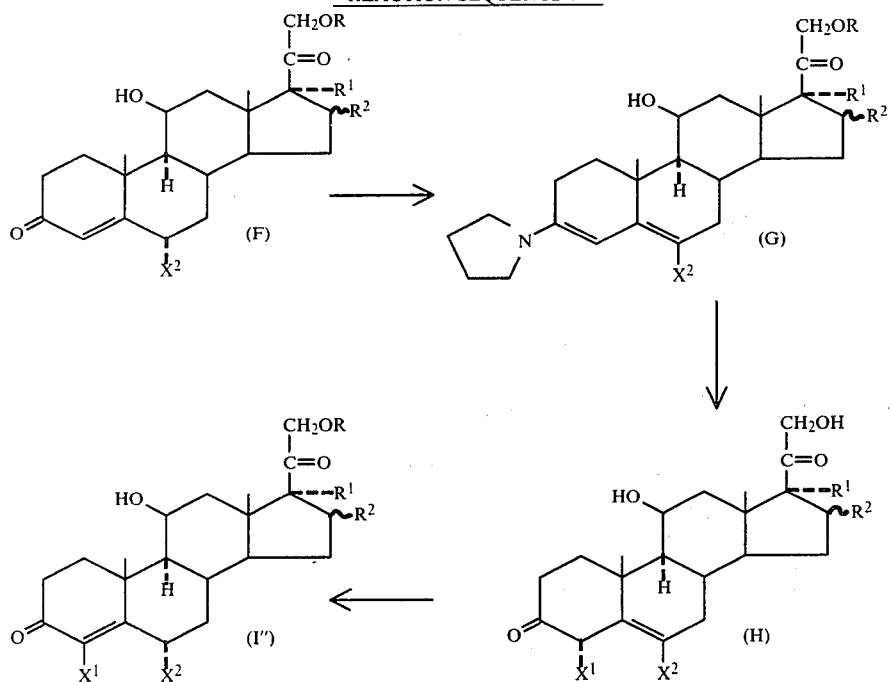

16α,17α-Isopropylidenedioxy-pregn-1,4,9(11)-trienes are readily prepared by reacting an 11β-hydroxy-9-unsubstituted-16α,17α-isopropylidenedioxypregna-1,4-diene with thionyl chloride in pyridine at 0° C. A 17α-hydroxy-pregna-1,4,9(11)-triene is prepared by reacting the corresponding 9-unsubstituted-11β,17α-dihydroxy-pregna-1,4-diene with methane sulfonyl chloride in pyridine with $SO_3$ at about 0° C. or with methyl chlorosulfinate (prepared by distilling methanol with thionylchloride) in tetrahydrofuran and pyridine at −78° C. and allowing the reaction mixture to slowly warm to ambient temperature.

An 11β-hydroxy (9-unsubstituted) steroid is readily prepared from a 3-keto-6α-substituted-pregna-1,4-diene or pregn-4-ene by methods well known in the art such as employing *Cunninghamella blakesleeana, Cunninghamella bainieri, Curvularia lunata,* or other suitable micro-organisms in a medium which selectively afford the desired 11β-hydroxy steroid.

In Reaction Sequence 2, the pregna-1,4,9(11)-trienes represented by formula (A) are converted to various intermediates by means known in the art. For example they are treated with chlorine according to the process of U.S. Pat. No. 3,009,933 to give the corresponding 9α,11β-dichloropregna-1,4-diene. The 9α-bromo-11-hydroxy compound is prepared by reacting the appropriate pregna-1,4,9(11)-triene with N,N'-dibromohydantoin to form the 9α-bromo-11-hydroxy-pregna-1,4-diene which can be isolated and can, in turn, be reacted with sodium hydroxide to give the corresponding 9β,11β-epoxide. This compound is then treated with a hydrogen fluoride/urea complex according to the process set forth in U.S. Pat. No. 3,211,758 to Tarkoey to give the 9α-fluoro-11β-hydroxy compound. The 9α-chloro-11β-hydroxy compound is prepared by reacting the 9β, 11β-epoxide with hydrogen chloride in methylene chloride or by reacting the pregna-1,4,9(11)-triene with N,N'-dichloro-dimethylhydantoin.

In the next step of Reaction Sequence 2, a compound represented by formula (B) is reacted to form a compound of the formula (C) wherein Y is methoxy or ethoxy. Note that there is a 21-alkanoyloxy group which can be later hydrolyzed to the 21-hydroxy group. If there is an 11β-hydroxy group, it is preferable to protect it as well by acetylation or the like. Protection of both positions is readily accomplished by reacting the compound represented by (B) (if $X^5$ is

and R is H) with acetic anhydride in pyridine and triethyl amine in presence of catalytic amounts of dimethylamino pyridine at 10°–100° C., at room temperature, to give a compound represented by formula (Ba) wherein $R^3O$ and $R^4O$ are the same alkanoyloxy. Although protection is not needed in the case of an 11β-hydroxy group, it does improve the yield.

The compounds represented by formulas (D) and (E) are readily separated by column chromatography on silica gel.

Compound (D) is reacted with a suitable base such as an alkali metal carbonate, e.g., potassium carbonate, in a suitable oxygenated hydrocarbon solvent such as alkanol, e.g., methanol, under nitrogen to rearrange the 5(6) double bond to form the desired 4-fluoro(4-chloro or 4-bromo)-3-ketone-pregna-1,4-diene.

If appropriate, the protecting groups at the 11β,17α- or 21- positions are hydrolyzed using a suitable base under nitrogen if the treatment with, e.g., potassium carbonate is not sufficient. Generally, if $X^4$ is hydrogen,

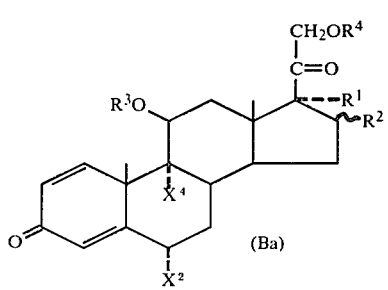

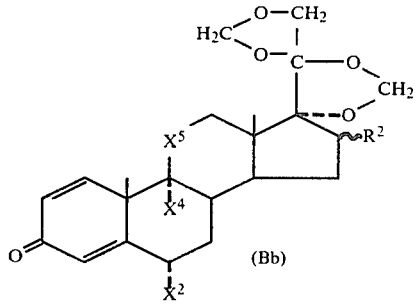

If compound (B) contains 17α,21-dihydroxy($R^1$ is OH and R is H) groups, it is preferably reacted with acid and aqueous formaldehyde to form the 17α,20; 20,21-bis methylenedioxy compound of formula (Bb). Thus both the 17α- and 21-hydroxy moieties are protected from reaction. Once the hydroxy groups, if any, are protected, compound (B), (Ba) or (Bb) is reacted with, for example, a large molar excess of trimethyl orthoformate in methanol or triethyl orthoformate in ethanol in the presence of a catalytic amount of a suitable acid catalyst, such as fuming sulfuric acid, at reflux temperature or less. About 50°–55° C. is preferred. Generally the molar ratio of trimethyl orthoformate is about 10:1 to about 30:1. Once the reaction is complete a base is added to neutralize the acid, and the resulting enol-ether represented by formula (C), where Y is methoxy or ethoxy, is recovered and purified using methods well known in the art such as evaporation, recrystallization, etc.

The enol ether represented by formula (C) is then fluorinated, chlorinated or brominated using perchloryl fluoride ($ClO_3F$) or trifluoromethoxy fluoride ($CF_3OF$) as a fluorinating agent, a source of positive chlorine such as N-chlorosuccinimide, dichlorohydantoin, etc. as a chlorinating agent, or a source of positive bromine such as dibromohydantoin to form the 3-keto-4α-fluoro (chloro or bromo)-pregna-1,5-diene represented by formula (D) or the 6α,6-difluoro-pregna-1,5-diene represented by formula (E).

In the case of $ClO_3F$, which is a gas, an approximately equimolar amount (1 to 1.1 moles $ClO_3F$ per mole compound C) is metered in to a mixture of compound (C) in a solution containing a major amount of acetone, preferably 90% by weight, and a minor amount of water, preferably about 10% over a period of about 1–3 hours at 10°–30° C., preferably ambient temperature. Dichlorohydantoin or dibromohydantoin are similarly reacted using suitable solutions.

hydrolysis of the 11β-acetoxy group requires sodium hydroxide in methanol. If, on the other hand, $X^4$ is fluoro, chloro or bromo, potassium carbonate is generally sufficient. Where there is a 9,11-bromhydrin or a 9,11-chlorhydrin, treatment with potassium carbonate may cause the formation of the 9,11-epoxide. In such a case, the epoxide is refluxed with hydrobromic acid or hydrochloric acid in chloroform or dichloromethane to reform the 9,11-bromhydrin or chlorhydrin. The BMD compound is hydrolyzed using a suitable acid such as 60% formic acid or 48% hydrofluoric acid.

Once the compound is obtained which is a 3-keto-pregna-1,4-diene (I′), the compound may be readily selectively hydrogenated across the 1,2-double bond by any of the suitable means known in the art to obtain the corresponding 3-keto-pregn-4-ene may be treated according to the process of this invention.

In Reaction Sequence 3, the starting compound is a 3-keto-pregn-4-ene represented by formula (F) which is first reacted with a suitable amine such as pyrrolidine to form an enamine represented by formula (G). This reaction takes place readily at reflux temperatures in a suitable inert organic solvent such as benzene or methanol.

The enamine represented by formula (G) is then fluorinated, chlorinated or brominated according to the procedure set forth above to form the 4α-fluoro(chloro or bromo)-3-keto-pregn-5-ene of formula (H) which then is treated with, for example potassium carbonate in methanol, to rearrange the double bond to the 4-position thus giving a compound of this invention represented by (I″). The resulting 3-keto-pregn-4-ene is readily dehydrogenated at the 1-position by methods known in the art such as using 2,3-dichloro-5,6-dicyano-1,4-benzoquinone in dioxane. Any protecting groups at the 11β, 17α, or 21 position are readily hydrolyzed by methods discussed hereinbefore.

In general, a 16α,17α-isopropylidenedioxy group is readily introduced by treating the corresponding 16α,17α-dihydroxy steroid with acetone in the presence of perchloric acid. The 16α,17α-dihydroxy groups are introduced by treating a pregn-16-ene derivative with potassium permanganate, acetone and acetic acid.

A 16-methyl group is introduced by treating the corresponding 20-keto-pregn-16-ene steroid with methyl magnesium bromide in the presence of cuprous chloride in an ether such as tetrahydrofuran. The 20-keto-pregn-16-ene steroid is prepared by preparing the 3,20-bis-semicarbazone of a 3,20-diketo-17α-hydroxy steroid, treating it with glacial acetic acid and acetic anhydride and then allowing the resulting product to react with aqueous pyruvic acid.

The 17α-hydroxy group is introduced in conjunction with the 16α-methyl group by first treating the corresponding 16-methyl-pregn-16-ene steroid (which is prepared by treating the corresponding pregn-16-ene steroid with diazomethane and then heating the resulting product to 180° C.) followed by treatment of the so formed 16 methyl-pregn-16-ene with hydrogen peroxide, in an aqueous basic media, and then permitting the resulting 16,17-oxido-16-methyl steroid to react with hydrogen bromide in glacial acetic acid. The resulting 17α-hydroxy-pregn-15-ene is hydrogenated with the use of a palladium catalyst to afford the corresponding 16α-methyl-17α-hydroxy derivative.

The 6-fluoro or 6-chloro starting steroids can be prepared by conventional techniques well-known to the art from steroids such as 17α-hydroxyprogesterone or hydrocortisone. For example, the 6-fluoro group is introduced by treating a 3-methoxy-pregna-3,5-diene (prepared by reacting a pregna-4-ene-3-one with trimethyl orthoformate in methanol) with perchloryl fluoride in dimethylformamide. See U.S. Pat. Nos. 2,983,737; 2,983,739; 3,053,838; 3,057,858; 3,124,251; 3,126,375; 3,201,391 and 3,248,389 for other examples.

Further specific embodiments of the process of this invention are found in the following Examples which are given by way of illustration only and not to be interpreted as limiting the scope of the claims appended hereto.

EXAMPLE 1

This example sets forth a process for preparing 16α,17α-isopropylidenedioxy-3-oxoandrosta-1,4-diene 17β-carboxylic acid according to the following reaction sequence wherein $X^1$ may be hydrogen, fluoro, chloro or bromo; $X^2$ is hydrogen, fluoro, chloro or methyl; $X^3$ is hydrogen or is fluoro when $X^2$ is fluoro; $X^4$ is hydrogen, fluoro, chloro or bromo; and $X^5$ is

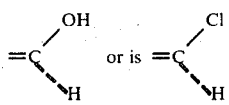

when $X^4$ is chloro:

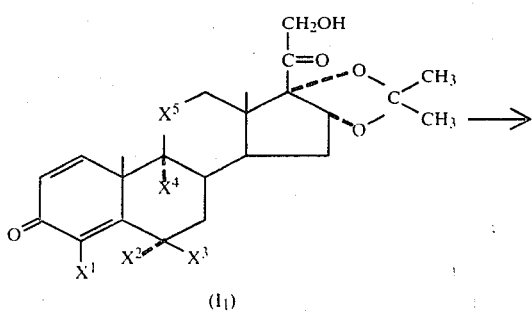

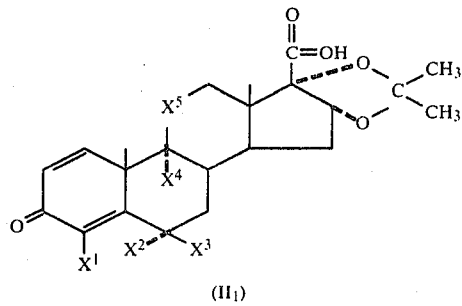

A. Preparation of 6α,9α-difluoro-11β-hydroxy-16α,17α-isopropylidenedioxy-3-oxoandrosta-1,4-diene 17β-carboxylic acid.

Twenty-five grams of fluocinolone acetonide (the compound of Formula (I) wherein $X^1$ and $X^3$ are hydrogen, $X^2$ is fluoro, $X^4$ is fluoro, $X^5$ is

and R' and $R^2$ are

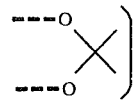

are added to 500 milliliters (ml) of methanol and 500 ml of methylene chloride ($CH_2Cl_2$) and 25 grams (g) of anhydrous potassium carbonate. The mixture is stirred while a current of air was bubbled through the solution for a period of 24 hours. The mixture is diluted with about 500 ml of water and concentrated under reduced pressure to about 250 ml. The solution is slowly acidified with concentrated hydrochloric acid to a pH of 2. The resulting crystalline precipitate is collected by filtration and dried to give 23.9 g of 6α,9α-difluoro-11β-hydroxy-16α,17α-isopropylidenedioxy-3-oxoandrosta-1,4-diene 17β-carboxylic acid, melting point (mp) 297°–300° C.

B. By following in principle the procedure set forth in Part A of this example but substituting a suitable starting material for fluocinolone acetonide, the following compounds are prepared:

9α,11β-dichloro-6α-fluoro-16α,17α-isopropylidenedioxy-3-oxoandrosta-1,4-diene 17β-carboxylic acid;

9α-chloro-6α-fluoro-11β-hydroxy-16α,17α-isopropylidenedioxy-3-oxoandrosta-1,4-diene 17β-carboxylic acid;

9α,11β-dichloro-4,6α-difluoro-16α,17α-isopropylidenedioxy-3-oxoandrosta-1,4-diene 17β-carboxylic acid;

4,6α,9α-trifluoro-11β-hydroxy-16α,17α-isopropylidenedioxy-3-oxoandrosta-1,4-diene 17β-carboxylic acid;

9α-chloro-4,6α-difluoro-11β-hydroxy-16α,17α-isopropylidenedioxy-3-oxoandrosta-1,4-diene 17β-carboxylic acid;

4-chloro-6α,9α-difluoro-11β-hydroxy-16α,17α-isopropylidenedioxy-3-oxoandrosta-1,4-diene 17β-carboxylic acid;

4,9α,11β-trichloro-6α-fluoro-11β-hydroxy-16α,17α-isopropylidenedioxy-3-oxoandrosta-1,4-diene 17β-carboxylic acid;

6α,9α,11β-trichloro-4-fluoro-11β-hydroxy-16α,17α-isopropylidenedioxy-3-oxoandrosta-1,4-diene 17β-carboxylic acid;

6α-chloro-4,9α-difluoro-11β-hydroxy-16α,17α-isopropyllidenedioxy-3-oxoandrosta-1,4-diene 17β-carboxylic acid;

4,6α-dichloro-9α-fluoro-11β-hydroxy-16α,17α-isopropylidenedioxy-3-oxoandrosta-1,4-diene 17β-carboxylic acid;

4,6α,9α,11β-tetrachloro-11β-hydroxy-16α,17α-isopropylidenedioxy-3-oxandrosta-1,4-diene 17β-carboxylic acid;

9α-fluoro-11β-hydroxy-6α-methyl-16α,17α-isopropylidenedioxy-3-oxoandrosta-1,4-diene 17β-carboxylic acid;

9α,11β-dichloro-6α-methyl-11β-hydroxy-16α,17α-isopropylidenedioxy-3-oxoandrosta-1,4-diene 17β-carboxylic acid;

4-chloro-9α-fluoro-11β-hydroxy-6α-methyl-16α,17α-isopropylidenedioxy-3-oxoandrosta-1,4-diene 17β-carboxylic acid;

9α,11β-dichloro-4-fluoro-6α-methyl-11β-hydroxy-16α,17α-isopropylidenedioxy-3-oxoandrosta-1,4-diene 17β-carboxylic acid;

4,9α-difluoro-11β-hydroxy-6α-methyl-16α,17α-isopropylidenedioxy-3-oxoandrosta-1,4-diene 17β-carboxylic acid;

6α,6β,9α-trifluoro-11β-hydroxy-16α,17α-isopropylidenedioxy-3-oxoandrosta-1,4-diene 17β-carboxylic acid; etc.

C. Ten (10) g of 6α,9α-difluoro-11β-hydroxy-16α,17α-isopropylidenedioxy-3-oxoandrosta-1,4-diene 17β-carboxylic acid prepared in the manner set forth in Part A is dissolved in 100 ml of dimethylformamide and 35 g of sodium bicarbonate along with 35 g of methyl iodide is added. The reaction mixture is stirred at room temperature for 48 hours. Then the mixture is diluted with water up to 3 liters (l). The crystalline precipitate obtained is collected by filtration then dissolved in 500 ml of CH$_2$Cl$_2$, dried over anhydrous sodium sulfate and filtered through a column of 200 g of silica gel, eluting first with 100% CH$_2$Cl$_2$, then 2, 4, 6 and 10% ethylacetate in CH$_2$Cl$_2$. The eluates are combined and concentrated to dryness under reduced pressure to give 9.5 g of methyl 6α,9α,difluoro-11β-hydroxy-16α,17α-isopropylidenedioxy-3-oxoandrosta-1,4-diene 17β-carboxylate, m.p. 235°–239° C., [α]$_D$ 34° (CHCl$_3$).

By following the above procedure but substituting the compounds made in Part B of this example the corresponding methyl 17-carboxylates are prepared.

By employing other alkyl iodides such as ethyl iodide, n-propyl iodide, isopropyl iodide, t-butyl iodide, and the like or phenyl iodide or benzyliodide other corresponding alkyl 17β-carboxylate of the compounds of Parts A and B of this invention are prepared.

EXAMPLE 2

This example sets forth a process for preparing compounds of the invention according to the following reaction sequence wherein X$^1$, X$^2$, X$^3$, X$^4$ and X$^5$ are defined as in Example 1, R is H or an alkanoyl group of 1–4 carbon atoms and there is a single or double bond between C-1 and C-2.

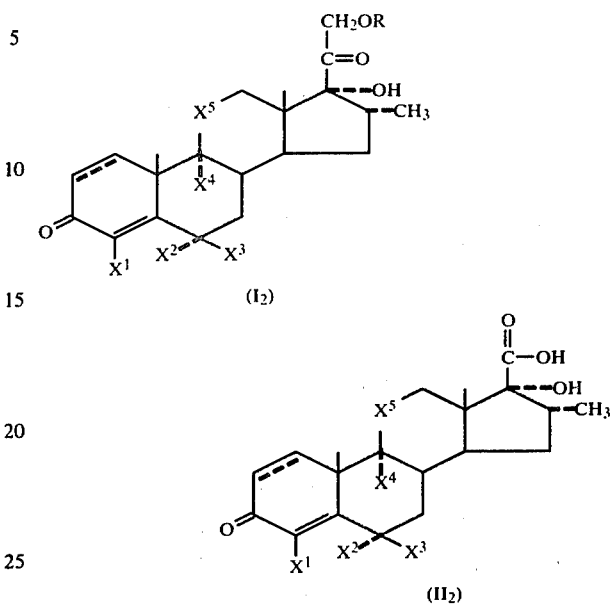

A. Preparation of 6α-fluoro-11β,17α-dihydroxy-16α-methyl-3-oxoandrostan-4-ene 17β-carboxylic acid.

Thirty-five grams of 21-acetoxy-6α-fluoro-11β,17α-dihydroxy-16α-methylpregn-4-ene-3,20-dione is mixed with 550 ml of methanol and 35 g of anhydrous potassium carbonate and stirred at room temperature and atmospheric pressure while a slow current of air is slowly bubbled through the solution for 22 hours. Methanol is added at intervals to maintain a constant volume. The reaction mixture is diluted with water to 1.5 l, then concentrated hydrochloric acid is added slowly to the mixture under magnetic stirring until a final pH of 2 is obtained. The resulting crystalline precipitate is collected by filtration and air dried to give 6α-fluoro-11β,17α-dihydroxy-16α-methyl-3-oxoandrost-4-ene-17β-carboxylic acid, mp 257°–260° C.

B. By following the procedure set forth in Part A of this example but substituting other appropriate starting materials the following compounds of this invention can be prepared:

9α,11β-dichloro-6α-fluoro-17α-hydroxy-16α-methyl-3-oxoandrosta-1,4-diene 17β-carboxylic acid;

6α,9α-difluoro-11β,17α-dihydroxy-16α-methyl-3-oxoandrosta-1,4-diene 17β-carboxylic acid, mp 289.5°–290° C.;

9α,11β-dichloro-4,6α-difluoro-17α-hydroxy-16α-methyl-3-oxoandrosta-1,4-diene 17β-carboxylic acid;

4,6α,9α-trifluoro-11β,17α-dihydroxy-16α-methyl-3-oxoandrosta-1,4-diene 17β-carboxylic acid;

9α-chloro-4,6α-difluoro-11β,17α-dihydroxy-16α-methyl-3-oxoandrosta-1,4-diene 17β-carboxylic acid;

4-chloro-6α,9α-difluoro-11β,17α-dihydroxy-16α-methyl-3-oxoandrosta-1,4-diene 17β-carboxylic acid;

4,9α,11β-trichloro-6α-fluoro-11β,17α-dihydroxy-16α-methyl-3-oxoandrosta-1,4-diene 17β-carboxylic acid;

6α,9α,11β-trichloro-4-fluoro-11β,17α-dihydroxy-16α-methyl-3-oxoandrosta-1,4-diene 17β-carboxylic acid;

6α-chloro-4,9α-difluoro-11β,17α-dihydroxy-16α-methyl-3-oxoandrosta-1,4-diene 17β-carboxylic acid;

4,6α-dichloro-9α-fluoro-11β,17α-dihydroxy-16α-methyl-3-oxandrosta-1,4-diene 17β-carboxylic acid;

4,6α,9α,11β-tetrachloro-17α-hydroxy-16α-methyl-3-oxoandrosta-1,4-diene 17β-carboxylic acid;

9α-fluoro-11β,17α-dihydroxy-6α,16α-dimethyl-17α-3-oxoandrosta-1,4-diene 17β-carboxylic acid;

9α,11β-dichloro-11β,17α-dihydroxy-6α,16α-dimethyl-3-oxoandrosta-1,4-diene 17β-carboxylic acid;

4-chloro-9α-fluoro-11β,17α-dihydroxy-6α,16α-dimethyl-3-oxoandrosta-1,4-diene 17β-carboxylic acid;

9α,11β-dichloro-4-fluoro-11β,17α-dihydroxy-6α,1-6α-dimethyl-3-oxoandrosta-1,4-diene 17β-carboxylic acid;

4,9α-difluoro-11β,17α-dihydroxy-6α,16α-dimethyl-3-oxoandrosta-1,4-diene 17β-carboxylic acid;

6α,6β,9α-trifluoro-11β,17α-dihydroxy-6α,16α-dimethyl-3-oxoandrosta-1,4-diene 17β-carboxylic acid; and the like.

C. The 17α-alkanoyl derivatives of the compounds made according to the procedure of Parts A and B are prepared as follows.

6α,9α-Difluoro-11β,17α-dihydroxy-16α-methyl-3-oxoandrosta-1,4-diene 17β-carboxylic acid is treated with 175 ml of pyridine and 175 ml of propionic anhydride, at room temperature for 3 hours. The mixture is slowly diluted with 1 l of water, stirred at room temperature for 1 hour and the precipitate collected by filtration. The aqueous mother liquor is extracted extensively with CH$_2$Cl$_2$ to get the desired product. The extracts are combined with the initial precipitate, the resulting solution dried over anhydrous sodium sulfate, filtered and concentrated to dryness under reduced pressure on a rotary evaporator to give 6α,9α-difluoro-11β-hydroxy-16α-methyl-3-oxo-17α-propionyloxyandrosta-1,4-diene-17β-carboxylic acid.

By following this procedure but substituting other compounds of Parts A or B of this example for 6α,9α-difluoro-11β,17α-dihydroxy-16α-methyl-3-oxoandrostane-4-ene-17β-carboxylic acid, the corresponding 17α-propionyloxy derivatives are obtained.

By substituting other anhydrides for propionic anhydride in this example, other 17α-alkanoyloxy derivatives of the compounds of this invention may be obtained.

D. 6α,9α-Difluoro-11β-hydroxy-16α-methyl-3-oxo-17α-propionyloxyandrosta-1,4-diene 17β-carboxylic acid made according to the process of Part C of this example is dissolved in 100 ml of dimethylformamide and treated with 35 g of sodium bicarbonate and 35 g of methyl iodide. The reaction mixture is stirred at room temperature for about 48 hours, then is diluted with water to make a mixture of having a total volume of 3 l. The crystalline precipitate so obtained is collected by filtration, dissolved in 500 ml of CH$_2$Cl$_2$ which solution is then dried over anhydrous sodium sulfate and filtered through a column of 200 g of silica gel. The column of silica gel is eluted first with 100% CH$_2$Cl$_2$, then 2, 4, 6 and 10% solutions of ethyl acetate in methanol are used as an eluant. The eluates are combined and concentrated to dryness under reduced pressure to yield 19.87 g of methyl 6α,9α-difluoro-11β-hydroxy-16α-methyl-3-oxo-17α-propionyloxyandrosta-1,4-diene 17β-carboxylate, m.p. 274°–275° C., [α]$_D$, 7° (CHCl$_3$).

Similarly, by employing other alkyl iodides in place of methyl iodide the corresponding alkyl 17β-carboxylates can be obtained.

E. Similarly, by following the procedure of Part D of this example but employing 17α-hydroxy compounds in place of the 17α-esters, the corresponding alkyl 17β-carboxylates having a 17α-hydroxy substituent are prepared.

EXAMPLE 3

By following in principle the procedure set forth in Example 2, Parts A through E, but starting with the corresponding 16β-methyl compounds in place of the 16α-methyl compounds, the corresponding 16β-methyl compounds of this invention may be obtained.

EXAMPLE 4

By following in principle the procedure set forth in Example 2, Parts A through E but substituting the corresponding 16-unsubstituted compound for the starting material in Example 2, the corresponding 16-unsubstituted compounds may be prepared.

EXAMPLE 5

This example sets forth a process for making the Δ$^4$ steroids of this invention represented by the formula

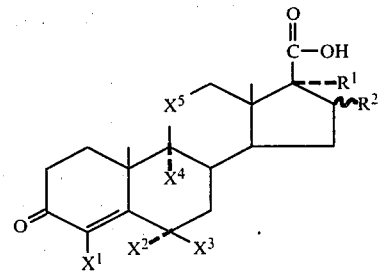

wherein X$^1$ through X$^5$ and R$^1$ and R$^2$ are as previously defined.

To a solution of 25 mg of tris-(triphenylphosphine)-chlororhodium in 6 ml of benzene and 15 ml of ethanol is stirred under hydrogen for 60 minutes. 6α-9α-Difluoro-11β-hydroxy-16α,17α-isopropylidenedioxy-3-oxoandrosta-1,4-diene 17-carboxylic acid (244 mg.) is added and the resulting solution is stirred under hydrogen at room temperature at atmospheric pressure. After hydrogen uptake is complete the solution is evaporated to dryness and the residue is taken up in a mixture of petroleum ether and methylene chloride. The pure product is isolated by column chromatography on silica gel to give 6α,9α-difluoro-11β-hydroxy-16α,17α-isopropylidenedioxy-3-oxoandrostan-4-ene 17β-carboxylic acid. Similarly, by substituting other Δ$^{1,4}$-steroids of this invention made according to examples 1–4 for the compound used above, in this example other corresponding Δ$^4$-steroids are prepared.

EXAMPLE 6

This example sets forth a process for preparing an 11-keto compound of this invention by oxidizing any of the 11β-hydroxy steroids set forth in Examples 1–5.

One g of 4,6α,9α,trifluoro-11β-hydroxy-16α-17α-isopropylidenedioxyandrosta-1,4-diene-3-one 17β-carboxylic acid dissolved in 50 ml of acetone and treated at room temperature with Jone's reagent (chromic anhydride in dilute sulfuric acid) dropwise until TLC indicates the absence of starting material. The mixture is treated with five drops of isopropyl alcohol to destroy any excess of reagent, then diluted with 50 ml of water and the mixture concentrated under vacuum under reduced pressure to give a crystalline material, namely 4,6α,9α-trifluoro-16α,17α-isopropylidenedioxyandrosta-1,4-diene-3,11-dione 17β-carboxylic acid.

Similarly by following in principle this procedure but substituting other compounds prepared according to Examples 1-5, other 11-keto steroids corresponding to the starting material employed are obtained.

What is claimed is:

1. A process for preparing etienic acids of the formula:

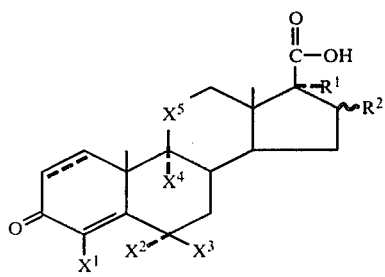

wherein $X^1$ $X^2$ and $X^3$ are each independently hydrogen, or fluoro; $X^4$ is hydrogen, fluoro or chloro; $X^5$ is

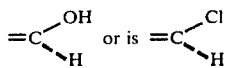

when $X^4$ is chloro; $R^1$ is α-hydroxy when $R^2$ is α-methyl or $R^1$ and $R^2$ together are 16α,17α-isopropylidenedioxy; and the broken and solid lines between C-1 and C-2 represent a single or double bond, which comprises reacting a compound represented by the formula:

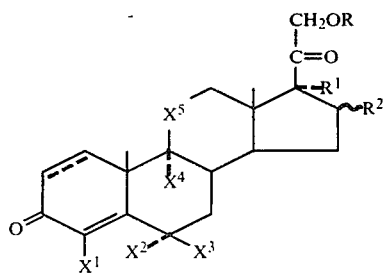

wherein

R is hydrogen or lower alkanoyl of 2-6 carbons or benzoyl and $X^1$, $X^2$, $X^3$, $X^4$, $X^5$, $R^1$ and $R^2$ are as described hereinbefore, with an alkali metal carbonate base in a lower alkanol in the presence of oxygen to form the corresponding compounds of formula II wherein $X^1$, $X^2$, $X^3$, $X^4$, $X^5$, $R^1$ and $R^2$ are as previously defined.

2. The process of claim 1 wherein said inorganic base is sodium carbonate or potassium carbonate and said lower alkanol is methanol.

3. The process of claim 1 wherein said reaction takes place in the presence of air.

4. The process of claim 2 wherein air is injected into the mixture of the lower alkanol, base and reactants.

5. The process of claim 1 wherein $R^1$ and $R^2$ together are 16α,17α-isopropylidenedioxy.

6. The process of claim 5 wherein $X^1$ is hydrogen, fluoro or chloro; $X^2$ is fluoro; $X^3$ is hydrogen; and $X^5$ is

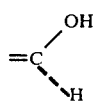

7. The process of claim 6 wherein $X^4$ is hydrogen or fluoro.

8. The process of claim 7 wherein $X^1$, $X^2$ and $X^4$ are all fluoro.

9. The process of claim 6 wherein $X^1$ is hydrogen.

10. The process of claim 1 wherein R is hydrogen or alkanoyl of two through six carbon atoms $R^1$ is hydroxy or alkanoyloxy of two through six carbon atoms, and $R^2$ is α-methyl.

11. The process of claim 10 wherein $X^1$ is hydrogen, fluoro or chloro; $X^2$ is hydrogen, fluoro or chloro; $X^3$ is hydrogen; $X^4$ is chloro and $X^5$ is

12. The process of claim 10 wherein $X^1$ and $X^3$ are each hydrogen, $X^2$ is fluoro, $X^4$ is hydrogen, fluoro or chloro, and $X^5$ is

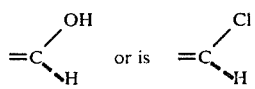

when $X^4$ is chloro.

13. The process of claim 12 wherein $X^4$ is fluoro.

14. The process of claim 12 wherein $X^4$ is hydrogen.